United States Patent
Kolditz et al.

(10) Patent No.: US 9,446,071 B2
(45) Date of Patent: Sep. 20, 2016

(54) ANTIMICROBIALLY ACTIVE COMPOSITIONS BASED ON ZINC COMPOUND, GLYCERINE MONOALKYL ETHER AND ANTIOXIDANT

(71) Applicant: L'AIR LIQUIDE SOCIETE ANONYME POUR L'ETUDE ET L'EXPLOITATION DES PROCEDES GEORGE, Paris (FR)

(72) Inventors: Petra Kolditz, Hamburg (DE); Klaus Weber, Hamburg (DE); Wolfgang Beilfuss, Hamburg (DE); Carsten Bungenstock, Hamburg (DE); Sabine Herweg, Norderstedt (DE)

(73) Assignee: L'AIR LIQUIDE SOCIETE ANONYME POUR L'ETUDE ET L'EXPLOITATION DES PROCEDES GEORGE CLAUDE, Paris (FR)

( * ) Notice: Subject to any disclaimer, the term of this patent is extended or adjusted under 35 U.S.C. 154(b) by 339 days.

(21) Appl. No.: 13/874,512

(22) Filed: May 1, 2013

(65) Prior Publication Data
US 2013/0309321 A1 Nov. 21, 2013

(30) Foreign Application Priority Data
May 16, 2012 (DE) ........................ 10 2012 208 291

(51) Int. Cl.
| | | |
|---|---|---|
| *A61K 33/32* | (2006.01) | |
| *A61K 33/30* | (2006.01) | |
| *A61K 8/34* | (2006.01) | |
| *A61K 8/67* | (2006.01) | |
| *A61K 31/08* | (2006.01) | |
| *A61K 31/315* | (2006.01) | |
| *A61K 8/27* | (2006.01) | |
| *A61Q 11/00* | (2006.01) | |
| *A61Q 17/00* | (2006.01) | |

(52) U.S. Cl.
CPC ................. *A61K 33/30* (2013.01); *A61K 8/27* (2013.01); *A61K 8/345* (2013.01); *A61K 8/678* (2013.01); *A61K 31/08* (2013.01); *A61K 31/315* (2013.01); *A61Q 11/00* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 8,058,218 B2 | 11/2011 | Beilfuss et al. | |
| 2006/0127430 A1 | 6/2006 | Gupta | |
| 2007/0218021 A1* | 9/2007 | Wells | 424/59 |
| 2008/0139507 A1 | 6/2008 | Gupta | |
| 2009/0130154 A1 | 5/2009 | Gupta | |
| 2010/0310487 A1* | 12/2010 | Beilfuss et al. | 424/65 |
| 2011/0091400 A1 | 4/2011 | Tesch et al. | |

FOREIGN PATENT DOCUMENTS

| | | |
|---|---|---|
| DE | 102004034691 A1 | 2/2005 |
| DE | 102006055040 A1 | 5/2008 |
| DE | 102007017851 | 10/2008 |
| DE | 102007024342 A1 | 11/2008 |
| DE | 102007038413 A1 | 2/2009 |
| FR | 2 915 679 | 11/2008 |
| WO | 2007142629 | 12/2007 |
| WO | 2008/006718 | 1/2008 |
| WO | 2008089822 | 7/2008 |
| WO | 2008/154395 | 12/2008 |
| WO | 2009/079135 | 6/2009 |

OTHER PUBLICATIONS

DE Office Action, dated Apr. 11, 2013, from corresponding 10 2012 208 291.3.

* cited by examiner

*Primary Examiner* — Snigdha Maewall
(74) *Attorney, Agent, or Firm* — Young & Thompson

(57) ABSTRACT

Antimicrobial compositions containing (i) at least one zinc compound selected from zinc salt and zinc oxide; (ii) at least one glycerine monoalkyl ether, $R-O-CH_2-CHOH-CH_2O$, wherein R is a branched or unbranched $C_1$-$C_{24}$ alkyl group that can be substituted with one or more hydroxy and/or $C_1$-$C_4$ alkoxy group(s) and/or the alkyl chain can be interrupted by up to four oxygen atoms; (iii) at least one antioxidant; and optionally (iv) one or more alkanediols; the weight ratio of (ii) to (iii) is at least 10:1. The compositions are used in cosmetics and pharmaceuticals and have broad anti-microbial activity, in particular against *Pseudomonas aeruginosa*, at active contents of only about 3 wt. %.

18 Claims, No Drawings

ANTIMICROBIALLY ACTIVE COMPOSITIONS BASED ON ZINC COMPOUND, GLYCERINE MONOALKYL ETHER AND ANTIOXIDANT

FIELD OF THE INVENTION

The present invention relates to antimicrobially active compositions which contain a zinc compound, a glycerine monoalkyl ether and an antioxidant. The compositions optionally also contain an alkane diol. Compositions according to the invention can be in concentrate form. The compositions are in particular used in cosmetic and pharmaceutical products (use formulation).

BACKGROUND OF THE INVENTION

The use of zinc compounds, glycerine monoalkyl ethers and alkanediols as additives for cosmetic and pharmaceutical products is known. The soothing and emulsifying properties of zinc compounds on the one hand and the skin moisturizing and solubilizing properties of glycerine monoalkyl ethers such as for example 2-ethylhexyl glycerine ether, especially in combination with alkanediols such as for example 1,2-octanediol, are reasons for the multiple possibilities for use in cosmetic and pharmaceutical preparations. A further advantage of the glycerine monoalkyl ethers such as 2-ethylhexyl glycerine ether is their physiological tolerability. 2-ethylhexyl glycerine ether is marketed by Schülke & Mayr GmbH, Norderstedt, German Federal Republic, as Sensiva® SC 50.

From DE 10 2007 017 851 A1, compositions are known which contain glycerine ethers, such as for example glycerine monoalkyl ethers, together with diol such as for example alkanediol, and/or polyol, and with good antimicrobial activity decrease or avoid whitening, prevent the skin drying out, regulate the moisture content and regrease the skin to an adequate extent.

US 2008/0139507 A1 describes a process for the treatment of skin diseases and changes, wherein certain clathrates of zinc zeolite with non-antibiotic organic active substances are applied locally.

US 2009/0130154 A1 relates to certain di- and multivalent metal zeolites, such as for example zinc zeolites, for the topical release of biological, skin- and haircare agents.

US 2006/0127430 A1 relates to the use of cage complexes of zeolites for the controlled topical release of organic cosmetic and pharmaceutical active substances, wherein the active substances can be present in the form of metal complexes such as for example zinc complexes.

WO 2009/079135 A2 relates to topical compositions which contain solid particles which are preferably formed of zinc oxide, titanium dioxide or both and are stabilized by means of enclosure by microspheres. Each of the microspheres contains a collapsed polymer shell, in which one or more solid particles are enclosed. The solid particles can be used either alone or in combination with other sunscreen agents, in order to make sunscreen compositions with a broader UV screening spectrum and increased stability to light.

FR 2 915 679 A1 describes a care product consisting of at least two separate aqueous compositions, wherein one composition contains a biologically active glass and the other a cosmetic or dermatological active substance. The latter can be a zinc salt for regulating the activity of the sebaceous glands.

The antimicrobial properties of selected zinc compounds in an aqueous or alcoholic medium against at least one microorganism are known. However, the antimicrobial action of such formulations is often limited to a few defined microorganisms, i.e. they do not have a broad antimicrobial action. Further, the possible uses of such formulations are severely limited because of the medium.

Further, combinations of zinc compounds with other antimicrobially active compounds are known from the state of the art. However, the additional anti-microbially active compounds are often toxicologically questionable. Thus for example isothiazolones are very irritant to the skin and mucous membranes and have marked allergenic potential. Many of these compounds thus do not meet the general legal conditions for the preservation of cosmetic and pharmaceutical products or are not suitable for use on dry skin or the skin of infants.

Zinc compounds and combinations thereof with additional antimicrobially active compounds also have the disadvantage that their antimicrobial activity is often not sufficient for the preservation of cosmetic and pharmaceutical products.

WO 2008/154395 A1 describes cleaning compositions which contain a cationic disinfectant, a film-forming cationic emulsifier, auxiliary solvents, a solvent system and optionally alkanediol. The compositions can also contain further antimicrobial active substances such as for example ethylhexyl glycerine ethers and a soothing quantity of zinc compound. Thus, inter alia, creams are described which contain several zinc compounds and alkanediols and ethylhexyl glycerine ethers, where the creams in addition to cationic disinfectants contain these active substances in a content of more than 5 wt. % overall, in order to have adequate antimicrobial activity.

WO 2008/006718 A2 relates to antimicrobial mixtures which contain one or more tropolones or tropolone derivatives and one or more further specific anti-microbial active substances. However, tropolones and derivatives thereof have the disadvantage that they inhibit the development of the spindle fibres, as a result of which cell division processes are hindered in the human body, which leads to serious poisoning phenomena and can be life threatening. The toxicity of this class of compounds markedly reduces their use in the production of cosmetic and pharmaceutical products.

WO 2007/142629 A1 relates to coatings of medical products which contain zinc compounds and antimicrobial active substances such as in particular chlorhexidine gluconate, and thus have a soothing action and prevent the transmission of infectious diseases. However, chlorhexidine leads to impairment of the sense of taste, to brownish deposits on teeth and tongue and to retardation of wound healing. In typical coating compositions, panthenol is contained. Panthenol contains a secondary amine/amide group, which is not desirable in certain formulations. In certain cases, irritation or contact allergies can occur as a result of the panthenol content. Accordingly, compositions which contain chlorhexidine gluconate or panthenol as essential components are not desirable.

Thus conventional formulations have inter alia the following disadvantages:
1. Their antimicrobial action is often limited to a few defined microorganisms.
2. In order to show sufficient antimicrobial activity, high concentrations of antimicrobial active substances are necessary.

3. They often contain antimicrobial active substances which are toxicologically questionable, so that they are unsuitable in particular for use in cosmetic and pharmaceutical products.
4. Their possible uses are often further severely limited because of their composition, e.g. the need for an aqueous or alcoholic medium.

SUMMARY OF THE INVENTION

Accordingly, the present invention is based on the problem of providing compositions which at low active substance concentrations already have broad anti-microbial activity, are toxicologically safe and have many possible uses.

This problem is solved by the antimicrobial composition according to claim 1. The composition according to the invention contains (i) at least one zinc compound, (ii) at least one glycerine monoalkyl ether, (iii) at least one antioxidant and optionally (iv) one or more alkanediols, where the weight ratio (w/w) of (ii) glycerine monoalkyl ether to (iii) antioxidant is at least 10:1.

The components (i) to (iii) and the optional component (iv) of the composition according to the invention have an outstanding synergistic antimicrobial action. Thus, surprisingly, low concentrations of the individual components already suffice for adequate activity of the composition against many different microorganisms, such as in particular *Pseudomonas aeruginosa*. The composition is toxicologically safe and can contain very different active substance concentrations, so that it has many possible uses.

Thus the invention relates to a composition which contains
(i) at least one zinc compound selected from zinc salt and zinc oxide,
(ii) at least one glycerine monoalkyl ether of the general formula

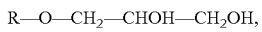

R—O—CH$_2$—CHOH—CH$_2$OH, wherein R is a branched or unbranched C$_1$-C$_{24}$ alkyl group, wherein the alkyl group can be substituted with one or more hydroxy and/or C$_1$-C$_4$ alkoxy group(s) and/or the alkyl chain can be interrupted by up to four oxygen atoms,
(iii) at least one antioxidant and
optionally
(iv) one or more alkanediols,
wherein the weight ratio (w/w) of component (ii), i.e. glycerine monoalkyl ether, to component (iii), i.e. antioxidant, is at least 10:1.

In the present application, alkanediol means an alkane which has two hydroxyl groups. Further, statements on weight ratios (w/w) and parts by weight of the components (i) to (iv) in the present application always relate to the total quantities of the particular components.

According to the invention, the zinc compound is preferably selected from the group consisting of zinc oxide, zinc chloride, zinc sulphate, zinc phosphate, zinc carbonate, zinc pyrithione, zinc ascorbate, zinc dehydracetate and zinc carboxylate, where the zinc carboxylate is preferably zinc lactate, zinc citrate, zinc stearate, zinc hydroxystearate, zinc benzoate, zinc sorbate, zinc salicylate, zinc gluconate, zinc ricinoleate, zinc undecylenate or zinc pyrrolidone-carboxylate. The zinc compound is in particular selected from the group consisting of zinc oxide, zinc chloride, zinc sulphate, zinc lactate, zinc citrate and zinc carbonate. Surface-modified zinc oxides can also be used, as disclosed in WO 2008/089822 A2.

DETAILED DESCRIPTION OF THE EMBODIMENTS

In all embodiments of the invention, it is preferred to use as component (i) a single water-soluble or a single water-insoluble zinc compound.

In one embodiment of the invention it is thus preferred that component (i) is zinc oxide. Alternatively, an embodiment is preferred wherein as component (i) a single zinc salt is used.

In one embodiment of the present invention, the alkyl chain of the glycerine monoalkyl ether is interrupted by up to 4 oxygen atoms, and is thus derived from an alcohol group which is accessible from an alcohol or diol by reaction with ethylene oxide and/or propylene oxide. In another embodiment, the alkyl group is a hydrocarbon group.

Thus the alkyl chain in the alkyl group R of the glycerine monoalkyl ether can contain alkylenoxy groups such as for example ethylenoxy and/or propylenoxy groups.

The alkyl group R preferably possesses 3 to 20 carbon atoms, more preferably 6 to 18 carbon atoms, in particular 8 to 12 carbon atoms, and most preferably 8 carbon atoms.

The alkyl group R is preferably selected from the group consisting of propyl, hexyl, 2-ethylhexyl, octyl, nonyl, decyl, menthyl, dodecyl, hexadecyl, octadecyl and octadecenyl. More preferably, the alkyl group R is 2-ethylhexyl or dodecyl, and especially preferably the alkyl group R is 2-ethylhexyl. Thus the especially preferred glycerine monoalkyl ether is 2-ethylhexyl glycerine ether.

The weight ratio (w/w) of (i) zinc compound to (ii) glycerine monoalkyl ether preferably lies in the range from 20:1 to 1:400, more preferably in the range from 10:1 to 1:200, in particular in the range from 5:1 to 1:100, and most preferably in the range from 3:1 to 1:10, or in the range from 1:10 to 1:80. In the description of the present invention, the quantity of zinc compound is in each case stated as anhydrous zinc oxide, unless otherwise stated.

According to the invention, the alkanediol is preferably a 1,2-alkanediol which has 2 to 18 carbon atoms, more preferably 3 to 14 carbon atoms, still more preferably 5 to 12 carbon atoms and especially preferably 6 to 10 carbon atoms. In particular, the alkanediol is selected from the group consisting of 1,2-hexanediol, 1,2-octanediol and 1,2-decanediol, the most preferred alkanediol being 1,2-octanediol.

The weight ratio (w/w) of (i) zinc compound to (iv) alkanediol preferably lies in the range from 1:50 to 5:1, more preferably in the range from 1:30 to 3:1 and in particular in the range from 1:10 to 1:1, wherein the quantity of zinc compound is stated as anhydrous zinc oxide.

The weight ratio (w/w) of (ii) glycerine monoalkyl ether to (iv) alkanediol is preferably 10:1 to 1:10, more preferably 5:1 to 1:5, still more preferably 4:1 to 1:4, still more preferably 3:1 to 1:3, in particular 2:1 to 1:3 and most preferably 1:1 to 1:3, for example about 3:7.

Antioxidants which are preferably used in the present invention are selected from the group consisting of 3-tert-butyl-4-hydroxyanisole, 2,6-ditert-butyl-p-cresol, tocopherol, in particular vitamin E, and derivatives thereof, in particular vitamin E derivatives such as vitamin E acetate, vitamin E linoleate, vitamin E nicotinate and vitamin E succinate, p-hydroxybenzoic acid esters, in particular the methyl, ethyl, propyl or butyl esters thereof, dimethyloldimethylhydantoin and N-acylamino acids and salts thereof, in particular N-octanoylglycine. The antioxidants are in particular selected from the group consisting of vitamin E and derivatives thereof, 3-tert-butyl-4-hydroxyanisole and 2,6-ditert-butyl-p-cresol, vitamin E being most preferred.

The tocopherols are particularly desirable antioxidants with regard to the uses of the compositions according to the invention in the production of cosmetics and pharmaceuticals which are subject to strictly drawn regulations and toxicity tests.

The weight ratio (w/w) of (ii) glycerine monoalkyl ether to (iii) antioxidant is preferably at least 100:1, more preferably at least 200:1, still more preferably at least 300:1, still more preferably at least 500:1, in particular at least 700:1 and most preferably at least 1000:1, for example about 2000:1. This ratio is preferably at most 1000000:1, more preferably at most 100000:1, still more preferably 50000:1, such as at most 20000:1, in particular at most 10000:1, and most preferably at most 5000:1.

Especially preferred according to the present invention is a composition which contains 2-ethylhexyl glycerine ether as (i) glycerine monoalkyl ether, vitamin E as (iii) antioxidant and 1,2-octanediol as (iv) alkanediol. Here the weight ratio (w/w) of 2-ethylhexyl glycerine ether to vitamin E is in particular about 2000:1. Most preferably, such a composition further contains the 2-ethylhexyl glycerine ether and the 1,2-octanediol in the weight ratio (w/w) of about 3:7.

The compositions according to the invention are preferably in the form of concentrates. Such a concentrate preferably contains
(i) 0.1 to 50 wt. %, preferably 0.5 to 40 wt. %, more preferably 1 to 35 wt. %, in particular 2 to 30 wt. % of zinc compound, where the quantity of zinc compound is stated as anhydrous zinc oxide,
(ii) 10 to 90 wt. %, preferably 10 to 70 wt. %, more preferably 10 to 50 wt. %, still more preferably 12 to 40 wt. %, in particular 14 to 30 wt. % of glycerine monoalkyl ether,
(iii) $10^{-4}$ to 0.9 wt. %, preferably 0.001 to 0.5 wt. %, more preferably 0.003 to 0.1 wt. %, still more preferably 0.005 to 0.05 wt. %, in particular 0.006 to 0.02 wt. % of antioxidant and
optionally
(iv) 10 to 90 wt. %, preferably 20 to 80 wt. %, more preferably 30 to 70 wt. %, in particular 33 to 65 wt. % of alkanediol,
wherein the weight ratio (w/w) of component (ii) glycerine monoalkyl ether to (iii) antioxidant is at least 10:1.

It is further preferred that the concentrate according to the invention as well as zinc compound, glycerine monoalkyl ether, antioxidant and optionally alkanediol contains no other components or at least is low in other components, i.e. it contains 30 wt. % or less, more preferably 10 wt. % or less of other components.

Low water content or water-free concentrates are especially preferred.

In a preferred embodiment, as well as the obligatorily specified components (i) zinc compound, (ii) glycerine monoalkyl ether and (iii) antioxidant, propylene glycol specifically is contained as (iv) alkanediol. In this embodiment, water and/or vaseline/oleogel-forming agent are contained as carrier material (namely additionally to (iv) propylene glycol or instead of (iv) propylene glycol).

When zinc oxide is used as the zinc compound, then 25 to 40 wt. % of vaseline are typically contained in a concentrate according to the invention.

Alternatively preferred are concentrates with 0.1 to 20 wt. % water, preferably 2 to 10 wt. % water.

Also preferred are concentrates with 70 to 1 wt. % propylene glycol, preferably 60 to 10 wt. % propylene glycol, and especially preferably 55 to 25 wt. % propylene glycol, such as 40 to 20 wt. % propylene glycol.

The present invention further relates to use formulations which contain the composition according to the invention, preferably in the form of the concentrate.

Such a use formulation then preferably contains
(i) 0.001 to 3.0 wt. %, preferably 0.002 to 2.0 wt. %, more preferably 0.01 to 1.0 wt. %, still more preferably 0.02 to 0.6 wt. % of zinc compound, where the quantity of zinc compound is stated as anhydrous zinc oxide,
(ii) 0.1 to 60 wt. %, preferably 0.1 to 20 wt. %, more preferably 0.3 to 10 wt. %, still more preferably 0.3 to 3 wt. %, in particular 0.5 to 1 wt. %, and most preferably about 0.6 wt. % of glycerine monoalkyl ether,
(iii) $10^{-6}$ to 0.6 wt. %, preferably $10^{-5}$ to 0.1 wt. %, more preferably $10^{-4}$ to 0.01 wt. %, still more preferably $10^{-4}$ to 0.001 wt. %, in particular 0.0003 wt. % of antioxidant and
optionally
(iv) 0.1 to 60 wt. %, preferably 0.3 to 20 wt. %, more preferably 0.5 to 10 wt. %, still more preferably 1 to 5 wt. %, in particular 1 to 2 wt. %, and most preferably about 1.4 wt. % of alkanediol,
wherein the weight ratio (w/w) of component (ii), glycerine monoalkyl ether to (iii) antioxidant, is at least 10:1.

The compositions according to the invention and in particular the use formulations according to the invention can further contain additives as further components, in particular further antimicrobial active substances and auxiliary agents.

The further antimicrobial active substances are for example
(a) aromatic alcohol, preferably phenoxyethanol, benzyl alcohol, phenethyl alcohol, phenylpropanol, phenylalkanol the alkyl group whereof has at least 4 carbon atoms, a phenol compound or a mixture thereof, in particular phenoxyethanol, benzyl alcohol or a mixture thereof,
(b) $C_1$-$C_4$ alcohol, preferably ethanol, propanol (isopropanol, n-propanol) or a mixture thereof,
(c) isothiazolone compound, preferably 1,2-benzisothiazol-3(2H)-one, methylisothiazolone, chloromethylisothiazolone, octylisothiazolone or a mixture thereof,
(d) oxidizing agent, preferably hydrogen peroxide,
(e) organohalogen, preferably 3-iodo-2-propynylbutyl carbamate (IPBC), 1,2-dibromo-2,4-dicyanobutane (DBDCB) or a mixture thereof,
(f) cationic active substance, preferably a quaternary ammonium compound such as for example benzalkonium salt or benzethonium salt, a biguanide compound such as for example alexidine, chlorhexidine or polyhexamethylene biguanide, ethyl lauroyl arginate hydrochloride, a bispyridinium compound such as for example octenidine or a mixture thereof, polyhexamethyleneguanide salts (such as polyhexamethyleneguanidinium chloride), oligo(2-(2-ethoxy)ethoxymethylguanidinium chloride) and
(g) polyglyceryl 2-laurate, polyglyceryl 2-caprate, polyglyceryl 3-dioleate, alkylglucosides such as lauryl, decyl or octylglucoside, gluconodeltalactone, glyceryl monolaurate, glyceryl caprylate, capryloyl and undecylenoylglycine, thymol, phenol compound, preferably o-phenylphenol, parabens or a mixture thereof.

The optional auxiliary substances are for example
(1) solvents or solubilizing agents, preferably water, alcohol, polyol with preferably at least three hydroxyl groups such as for example glycerine, glycol ether or a mixture thereof,
(2) skincare additive and/or moisture retention agent and/or softener, preferably allantoin, urea, amino acid, panthenol, hexyl laurate, cetearyl isononanoate, dicaprylyl ether, hexyl-decanol or a mixture thereof,
(3) complexing agents, preferably EDTA, biologically degradable complexing agents such as for example trisodium ethylenediamine disuccinate, ethylenediamine disuccinate and iminodisuccinate salts or a mixture thereof,
(4) salt, preferably sodium chloride, magnesium salt such as for example magnesium sulphate or a mixture thereof,
(5) buffer and/or alkalizing agent and/or acid, preferably alkali metal hydrogen carbonate, sodium hydroxide, potassium hydroxide, gluconolactone, citric acid, lactic acid or a mixture thereof,
(6) plant extract, for example hop extract,
(7) organic UV filter and/or inorganic UV filter, preferably titanium dioxide,
(8) emulsifier, preferably nonionic emulsifier, more preferably nonionic emulsifier based on polyethylene glycol (PEG), in particular PEG 30 dipolyhydroxystearate, PEG 7 hydrogenated castor oil or a mixture thereof,
(9) thickener, polymer, wax, oil, oleogel-forming agent, hydrocarbon gel such as for example vaseline or a mixture thereof, and
(10) analgesics, inflammation inhibitors or a mixture thereof.

Preferred auxiliary substances are water, glycerine, urea, hexyl laurate, cetearyl isononanoate, dicaprylyl ether, hexyldecanol, trisodium ethylenediamine disuccinate, magnesium sulphate, PEG 30 dipolyhydroxystearate, PEG 7 hydrogenated castor oil and vaseline.

The compositions and use formulations according to the invention can be present as solid, semisolid or liquid, gel-like or emulsion-like preparations.

The production of a composition according to the invention, in particular of a concentrate, is preferably effected by simple mixing of the components. For example, the glycerine monoalkyl ether is taken and the antioxidant, the alkanediol and the zinc compound added, preferably in that order, with stirring. Additives can also optionally be stirred in.

In a preferred embodiment, the zinc compound is previously dissolved in a small quantity of water or in a larger quantity of propylene glycol. The glycerine monoalkyl ether, which is typically already present in combination with antioxidant (and preferably also with alkanediol) is then added.

The production of a use formulation according to the invention can for example be effected by stirring a composition according to the invention, preferably in the form of a concentrate, into an appropriate quantity of additive or a combination of two or more additives and thus diluting it. A use formulation according to the invention can also be produced by adding appropriate quantities of zinc compound, glycerine monoalkyl ether, antioxidant and optionally alkanediol in any order to one or more additives (e.g. water, alcohols and/or polyols).

The compositions and use formulations according to the invention, in particular the use formulations according to the invention, can be present in the form of emulsions, for example in the form of water in oil emulsions. The production of such emulsions is for example effected as follows:

Typically
  an aqueous phase, which as well as water can contain one or more water-soluble zinc compounds (such as for example zinc chloride, zinc sulphate or zinc lactate) and other additives (wherein polyols such as for example glycerine or salts such as for example magnesium sulphate are preferred),
  is stirred into an oily phase, which as well as emulsifier and other additives (wherein skincare additive and/or moisture retention agents and/or softeners are preferred) can contain one or more water-insoluble zinc compounds (such as for example zinc oxide),
  in order to produce an aqueous and/or oily mixture with a content of water-soluble zinc compound and/or water-insoluble zinc compound, and
  this mixture is then homogenized, preferably by stirring at a few thousand rpm, for example at 10,000 rpm. Next a mixture of glycerine monoalkyl ether, antioxidant and optionally alkanediol is stirred into the resulting emulsion.

Typically, the compositions, if they are used in the form of the concentrate, are introduced in a quantity of 0.1 to 20 wt. %, preferably in a quantity of 0.5 to 15 wt. %, preferably 1 to 10 wt. %, more preferably 1 to 5 wt. %, and in particular 2 to 4 wt. %, to give the use formulations.

Surprisingly, the zinc compound, the glycerine monoalkyl ether and the antioxidant as components of the compositions according to the invention have such an outstanding synergistic antimicrobial action, in particular if alkanediol is also present, that the compositions and use formulations according to the invention already have sufficient activity against many different microorganisms when the said components are contained therein in a total content of only about 3 wt. % overall. The compositions and use formulations according to the invention are for example anti-microbially active against gram positive bacteria such as for example staphylococci, in particular *Staphylococcus aureus* such as MRSA, and enterococci, in particular vancomycin-resistant enterococci, and gram negative bacteria such as for example *Pseudomonas aeruginosa*, non-enveloped viruses and protozoa. They are especially suitable for the control of *Pseudomonas aeruginosa*. A further microbe which is surprisingly controlled according to the invention is *Streptococcus mutans*, a microbe which causes caries.

Since, as well as their antimicrobial activity, the compositions and use formulations according to the invention are distinguished by their toxicological safety, the present invention further relates to compositions and use formulations for use for the control of bacteria, yeasts, fungi, viruses and/or protozoa not only on non-living surfaces but also on living surfaces and use formulations for use for the treatment of a microbially caused disease. According to the invention, the treatment of a microbially caused disease is understood to mean both the control of the disease and also the moderation of the clinical picture of the disease. The diseases are in particular skin and mucous membrane diseases.

Because of their toxicological safety, the compositions according to the invention, especially concentrates, can be used not only in technical, but above all also in cosmetic and/or pharmaceutical products.

Accordingly, the use formulations according to the invention can be cosmetic or pharmaceutical products. Such cosmetic or pharmaceutical products are for example deodorant preparations, foot care preparations such as for example foot deodorants, skincare preparations such as for example aftershaves or aftershave lotions, preparations for wet wipes, cosmetics for sensitive skin, antiacne agents, sunscreen preparations, oral preparations such as for example mouth rinse solutions, mouthwashes, toothpastes or agents against halitosis, or other agents for anti-bacterial mouth care, agents for hair treatment such as for example antidandruff agents, cosmetics based or partly based on natural raw materials, disinfectants for skin, hands and wounds, antiseptics, antimicrobial wash lotions, antimicrobially treated lubricants, stabilizers for cosmetic and/or pharmaceutical preparations and baby products. Further uses are the microbial stabilization of water-containing compositions such as leave-on or rinse-off products, for the antimicrobial treatment of polymeric materials such as cloths, for intensifying the efficacy of known antimicrobial active substances, and as perfume fixatives.

The invention offers the following advantages:

- The zinc compound, the glycerine monoalkyl ether, the antioxidant and (if present) the alkanediol have an outstanding synergistic antimicrobial action.
- The compositions and use formulations already have broad antimicrobial activity at active substance contents of about 3 wt. %.
- The compositions and use formulations are toxicologically safe.
- The compositions are suitable for the antimicrobial stabilization of cosmetic, pharmaceutical and technical products and products for antibacterial mouth care.
- The compositions have pronounced compatibility with constituents of cosmetic or pharmaceutical products.
- The compositions and use formulations have no skin irritant activity, but are soothing, reduce the stinging action of constituents of cosmetic products, have very good skin and mucous membrane tolerability, improve the skin feel, increase skin moisture and care for the skin.
- The compositions and use formulations aid wound healing.
- The compositions and use formulations are colourless/white to yellow, low odour and chemically largely inert.
- The premixed zinc compounds are well miscible with a mixture of glycerine monoalkyl ether and alkanediol, especially in the presence of water or propylene glycol. Thus according to the invention, compositions in the form of liquid concentrates with a content of zinc compound of up to 50 wt. % can be produced.
- The compositions have solubilizing properties towards further components.
- The compositions in the form of concentrates are heat- and cold-stable, typically in the range from −5° C. to 40° C.
- The compositions and use formulations are distinguished by good wetting of different surfaces. Living surfaces such as skin, mucous membrane, sensitive, dry, reddened, irritated skin, wounds, burns and flexible surfaces such as textiles, polymers and nonwovens, and hard surfaces such as metals, wood, plastics and ceramics are particularly well wetted.

The surprising effects achieved are illustrated by the following examples.

EXAMPLES

Meanings in the following examples are as follows:

| | |
|---|---|
| Dehymuls HRE 7 | PEG-7 hydrogenated castor oil, obtainable from Cognis |
| Arlacel P 135 | PEG-30 dipolyhydroxystearate, obtainable from Uniquema |
| Cetiol A | hexyl laurate, obtainable from Cognis |
| Cetiol SN | cetearyl isononanoate, obtainable from Cognis |
| Cetiol OE | dicaprylyl ether, obtainable from Cognis |
| Eutanol G16 | hexyldecanol, obtainable from Cognis |
| Mghs | PEG-40 macrogol glycerol hydroxystearate |
| TZC | trizinc citrate |

Key: EV=mixture of 2-ethylhexyl glycerine ether and vitamin E in the weight ratio of 2000:1, EVO=mixture of EV and 1,2-octanediol in the weight ratio of 3:7, and d.=days.

Method A—Microbial Count Reduction Test Method

Aim:

The aim of this microbial count reduction test is to identify suitable preservatives and exposure times for samples inoculated in the laboratory.

Solutions and Nutrient Media:

| | |
|---|---|
| CSA | (casein peptone - soya meal peptone - agar) |
| SA | (Sabouraud agar) |
| CSS | (casein peptone - soya meal peptone - solution) |
| Nad | (physiological cooking salt solution, 0.85%) |

Test Organisms:

| | |
|---|---|
| *Staphylococcus aureus* | ATCC 6538 |
| *Pseudomonas aeruginosa* | ATCC 15442 |
| *Candida albicans* | ATCC 10231 |
| *Aspergillus niger* | ATCC 6275 |

Additional Note: This test can also be performed with actual microbial samples or another specified microbe spectrum.

Cultivation and Production of Inoculation Solutions:

Bacteria:

24-hr CSS cultures are created from 24-hr CS slant agar cultures of *Staphylococcus aureus/Pseudomonas aeruginosa*. The incubation is performed at 37° C.

The titre of the bacterial suspensions is ca. $10^9$ CFU/ml.

Yeast:

A 4-day old *Candida albicans* culture (CSA+grape sugar/37° C.±1° C.) is washed out with 5 ml of physiological NaCl and adjusted according to a barium sulphate standard (see DVG Guideline). The titre of the *Candida albicans* suspension is $10^8$ CFU/ml.

Moulds:

A 7-14 day old *Aspergillus niger* culture on Sabouraud agar (25° C.±1° C.) is washed out with 5 ml of physiological NaCl, filtered through a glass funnel with glass wool and made up to 200 ml. This suspension has a titre of ca. $10^7$ CFU/ml.

Procedure:

The samples (e.g. emulsions) are treated with various concentrations of appropriate preservatives. A dilution series is needed for each test microbe. Then the samples are inoculated with the microbial suspensions and stirred well:
25 g samples=0.1 ml microbial suspension
50 g samples=0.2 ml microbial suspension After defined exposure times, the samples are plated out onto CSA or Sabouraud agar with sterile glass rods. The samples inoculated with bacteria were plated out onto CSA and incubated for 48 hrs at 37° C. The samples inoculated with yeasts or moulds were plated out onto Sabouraud agar and incubated for 48 hrs at 37° C. (*Candida albicans*) and 25° C. (*Aspergillus niger*).

Assessment:
−=no growth
+=weak growth
++=moderate growth
+++=strong growth
++++=massive growth
R=turf-like growth Method B—Determination of the Preservative Action of Chemical Preservatives in Cosmetic Formulations (Koko Test)

Principle:

By means of the method described, the activity of chemical preservatives as regards pack preservation for cosmetic formulations is tested. For this, the preservatives to be tested are added in various test preparations to the unpreserved samples. An ongoing microbial burden is achieved by periodical inoculation of the test preparations. Parallel to the inoculation, plating out of the individual preparations is effected directly beforehand each time. An assessment is made in terms of the microbial growth of the smears. The longer the period until the first occurrence of microbial growth is, the more effective is the preservative.

Solutions and Nutrient Media
CSA (casein peptone-soya meal peptone-agar) Oxoid CM 131
SA (Sabouraud agar) Oxoid CM 41
Sterile 0.85% (w/v) NaCl solution
Test Organisms

| Bacteria | |
| --- | --- |
| *Kocuria rhizophila* | ATCC 9341 |
| *Staphylococcus aureus* | ATCC 6538 |
| *Enterobacter gergoviae* | ATCC 33028 |
| *Escherichia coli* | ATCC 11229 |
| *Klebsiella pneumoniae* | ATCC 4352 |
| *Pseudomonas aeruginosa* | ATCC 15442 |
| *Pseudomonas fluorescens* | ATCC 17397 |
| *Pseudomonas putida* | ATCC 12633 |
| Yeasts | |
| *Candida albicans* | ATCC 10231 |
| Moulds | |
| *Aspergillus niger* | ATCC 6275 |
| *Penicillium funiculosum* | ATCC 36839 |

Cultivation of the Test Organisms

The bacteria are each evenly plated out over the whole surface of a CS nutrient medium with a sterile glass rod for each and incubated for 24 hrs at 30±1° C. The yeast *C. albicans* is plated onto a Sabouraud nutrient medium with a sterile glass rod and incubated for 48 hrs at 30±1° C.

The laboratory cultures of the bacteria and of the yeast *C. albicans* are renewed every 4 weeks.

The moulds *A. niger* and *P. funiculosum* are plated out onto one (*A. niger*) or two (*P. funiculosum*) Sabouraud plates (which contain 100 µg/ml gentamycin and 50 µg/ml chloramphenicol) with a sterile glass rod and incubated for 7 to 14 days at 25±2° C.

The laboratory cultures of the moulds *A. niger* and *P. funiculosum* are transferred every 3 weeks.

The stock cultures are renewed every 12 months.

Preparation of the Starting Mould Suspensions

For the preparation of the mixed suspensions, starting suspensions of *A. niger* and *P. funiculosum* are firstly prepared:

*Aspergillus niger*:

A 7 to 14-day old Sabouraud plate is washed off with 10 ml (2×5 ml) of sterile 0.85% NaCl solution (w/v). The washed off fungal suspension is passed through a filter with glass wool (sterile) into a sterile 100 ml measuring cylinder and made up to 100 ml with sterile 0.85% NaCl solution. The *A. niger* suspension thus obtained is then transferred into a sterile glass-stoppered bottle with sterile glass beads.

Titre of *A. niger* suspension: ca. $10^7$ CFU/ml.

*Penicillium* funiculosum:

Two 7 to 14-day old Sabouraud plates are washed off with 10 ml (2×5 ml) of sterile 0.85% NaCl solution (w/v). The washed off fungal suspensions are passed through a filter with glass wool (sterile) into a sterile 100 ml measuring cylinder and made up to 100 ml with sterile 0.85% NaCl solution. The *P. funiculosum* suspension thus obtained is then transferred into a sterile glass-stoppered bottle with sterile glass beads.

Titre of *P. funiculosum* suspension: ca. $10^{6-7}$ CFU/ml.

The mould suspensions prepared as described above are kept for 3 weeks in the refrigerator at 5° C.±2° C. and can be used within this time. Before use for the preparation of the mixed suspension, the mould suspensions must be briefly shaken up in order to obtain a homogeneous suspension.

A check of the titres of the starting mould suspensions is performed at least quarterly.

Preparation of the Mixed Suspensions

For the preparation of the mixed suspensions, the bacteria, one plate per strain, are washed off with ml of sterile 0.85% NaCl solution per CSA plate, filtered through a sterile glass funnel with glass wool (sterile) and made up to 150 ml with 0.85% NaCl solution. This bacterial suspension has a titre of ca. $10^{10}$ CFU/ml.

The yeast *C. albicans* is likewise washed off from a Sabouraud plate with 10 ml of sterile 0.85% NaCl solution and filtered through a sterile glass funnel with glass wool (sterile). To this suspension are added 10 ml of the mould suspension (*A. niger* and *P. funiculosum*) prepared as described above. 3 ml of the bacterial suspension prepared as described above (titre ca. $10^{10}$ CFU/ml) are added. The resulting mixed suspension is made up to 150 ml with 0.85% NaCl solution.

The bacterial titre of the mixed suspension is ca. $10^8$ CFU/ml. The titre for *C. albicans* in the mixed suspension is ca. $10^8$ CFU/ml. The titre for *A. niger* and *P. funiculosum* in the mixed suspension is ca. $10^6$ CFU/ml.

A check of the titres in the mixed suspension is performed at least quarterly.

Procedure 25 or 50 g of the material to be preserved is treated in separate preparations with different concentrations of the preservative to be tested. As a growth control, a non-preserved product sample is used in each case.

The test preparations are plated out once weekly onto CS and Sabouraud nutrient media, the first plating out being performed immediately before the new inoculation; these are then inoculated with the mixed suspension (with 0.1 ml for 25 g samples, with 0.2 ml for 50 g samples). The inoculated samples are incubated at 25° C.±2° C. over the whole test period.

The assessment of the microbial growth of the smears incubated at 25° C.±2° C. is performed after 3 to 4 days. For safety, negative smears are observed for a further days and assessed again. The assessment of the preservative action of the individual product concentrations is performed in a semi-quantitative method via the growth of the individual smears:

−=no growth ++=moderate growth
+=weak growth +++=strong growth

The growth is differentiated according to bacteria (B), yeasts (Y) and moulds (M). The test is usually performed over 6 inoculation cycles or discontinued after massive growth (+++) is seen twice.

If growth can be detected in neither the preserved samples nor the non-preserved product samples (blank) after five successive inoculation cycles, then the inoculation in the sixth inoculation cycle is performed with five times the quantity of the mixed suspension (0.5 ml for 25 g samples, 1 ml for 50 g samples).

Assessment of the Results

A preservative is to be assessed as good if under the aforesaid laboratory conditions there is a period of weeks without microbial infection of the sample preparations, i.e. no microbial growth is detectable even after the sixth microbial inoculation.

Method C (MIC)

The minimal inhibitory concentration which is required by a preparation in order to inhibit the growth of a defined microorganism is tested.

Procedure 5 ml of the given product test solution (optionally doubly concentrated) is mixed with 5 ml of doubly concentrated CSS broth. The tubes are then inoculated with 0.1 ml of a test suspension containing $10^8$ microbes.

Incubation

The assessment is performed after 48 hr incubation at 36° C.±1° C. (*C. albicans* 30° C.±1° C.).

Assessment

The highest dilution of the product in CSS broth which inhibits the growth of the test organisms after 48 hrs such that it does not lead to clouding of the suspension (+=growth of the microorganisms, −=no growth of the microorganisms) serves as the measure of the proliferation-inhibiting efficacy (inhibitory concentration).

Example 1

The antimicrobial activity of use formulations according to the invention against the gram negative bacterium *Pseudomonas aeruginosa* should be tested by the microbial count reduction method (Method A). For this, use formulations in the form of water in oil lotions, i.e. water in oil emulsions, which contain the EVO and a different weight content of zinc oxide, zinc chloride, zinc sulphate or zinc lactate, were used. These were prepared as follows:

2.00 g of Arlacel P 135 were heated to about 70° C. and added to an oily phase which consists of 9.50 g of Dehymuls HRE 7, 13.00 g of Cetiol A, 15.25 g of Cetiol SN, 13.00 g of Cetiol OE, 6.25 g of Eutanol G 16 and—if the zinc compound is zinc oxide—zinc oxide. Next, as the aqueous phase, a solution of 12.50 g of glycerine (85 wt. %), 2.50 g of magnesium sulphate heptahydrate ($MgSO_4.7H_2O$) and—if the zinc compound is zinc chloride, zinc sulphate or zinc lactate—zinc chloride, zinc sulphate heptahydrate or zinc lactate trihydrate in fully deionized water was added to the oily phase with stirring at 250 rpm. For this, the quantity of water was always selected such that the total quantity of the resulting two-phase system was 247.50 g. The pH of the aqueous phase used was about 5.0 in each case, and with the use of zinc lactate trihydrate it was adjusted to 5.2 with sulphuric acid. The system was then homogenized for 2 mins at 10,000 rpm and the resulting emulsion stirred for 15 mins at 100 rpm. 120.00 g of the emulsion were then taken out, treated with 2.40 g of EVO and again stirred for 15 mins at 100 rpm.

The composition of the use formulations is listed in Table 1. The content by weight of the zinc compound here is in each case based on the form of the zinc compound used, i.e. on $ZnO$, $ZnCl_2$, $ZnSO_4.7H_2O$ or $Zn(COO\!-\!CHOH\!-\!CH_3)_2.3H_2O$. Also stated are the corresponding quantities calculated on ZnO as reference quantity.

The antimicrobial activity of the use formulations according to the invention from Table 1 were tested in the microbial count reduction test (method A). For this, they were each inoculated with 0.25 ml of a *Pseudomonas aeruginosa*-containing suspension and the microbial count determined after 24 hrs, 48 hrs, 72 hrs and 168 hrs.

Surprisingly, the use formulations tested already no longer contained any *Pseudomonas aeruginosa* organisms after 24 hrs, as can be seen from Table 2. Hence through the combination of EVO with a great variety of zinc compounds in the use formulations according to the invention, a pronounced antimicrobial activity against *Pseudomonas aeruginosa* can be achieved, and this can already be achieved with a content of only 2.0 wt. % of EVO and only 0.14 to 1.0 wt. % of zinc compound (the quantity of zinc compound being stated as anhydrous zinc oxide), i.e. with an active substance content of only 2 to 3 wt. % overall.

TABLE 1

| | | Content (wt. %) | | | | | | | | | |
|---|---|---|---|---|---|---|---|---|---|---|---|
| Sample | Zinc compound | Arlacel P 135 | Dehymuls HRE 7 | Cetiol A | Cetiol SN | Cetiol OE | Eutanol G 16 | EVO | Glycerine[a] | $MgSO_4$[b] | Quantity of zinc compound wt. %/wt. %[e] |
| A | ZnO | 0.8 | 3.8 | 5.1 | 6.0 | 5.1 | 2.5 | 2.0 | 5.0 | 1.0 | 0.25/0.25 |
| B | ZnO | 0.8 | 3.8 | 5.1 | 6.0 | 5.1 | 2.5 | 2.0 | 5.0 | 1.0 | 0.5/0.5 |
| C | ZnO | 0.8 | 3.8 | 5.1 | 6.0 | 5.1 | 2.5 | 2.0 | 5.0 | 1.0 | 1.0/1.0 |

TABLE 1-continued

| Sample | Zinc compound | Arlacel P 135 | Dehymuls HRE 7 | Cetiol A | Cetiol SN | Cetiol OE | Eutanol G 16 | EVO | Glycerine[a] | MgSO$_4$[b] | Quantity of zinc compound wt. %/wt. %[e] |
|---|---|---|---|---|---|---|---|---|---|---|---|
| D | ZnCl$_2$ | 0.8 | 3.8 | 5.1 | 6.0 | 5.1 | 2.5 | 2.0 | 5.0 | 1.0 | 0.25/0.15 |
| E | ZnCl$_2$ | 0.8 | 3.8 | 5.1 | 6.0 | 5.1 | 2.5 | 2.0 | 5.0 | 1.0 | 0.5/0.3 |
| F | ZnCl$_2$ | 0.8 | 3.8 | 5.1 | 6.0 | 5.1 | 2.5 | 2.0 | 5.0 | 1.0 | 1.0/0.6 |
| G | ZnSO$_4$[c] | 0.8 | 3.8 | 5.1 | 6.0 | 5.1 | 2.5 | 2.0 | 5.0 | 1.0 | 0.5/0.14 |
| H | ZnSO$_4$[c] | 0.8 | 3.8 | 5.1 | 6.0 | 5.1 | 2.5 | 2.0 | 5.0 | 1.0 | 1.0/0.28 |
| I | ZnSO$_4$[c] | 0.8 | 3.8 | 5.1 | 6.0 | 5.1 | 2.5 | 2.0 | 5.0 | 1.0 | 2.0/0.57 |
| J | Zn lactate[d] | 0.8 | 3.8 | 5.1 | 6.0 | 5.1 | 2.5 | 2.0 | 5.0 | 1.0 | 1.0/0.27 |
| K | Zn lactate[d] | 0.8 | 3.8 | 5.1 | 6.0 | 5.1 | 2.5 | 2.0 | 5.0 | 1.0 | 2.0/0.55 |

[a]85 wt. %,
[b]in form of the heptahydrate,
[c]in form of the heptahydrate,
[d]in form of the trihydrate,
[e]calculated as ZnO

TABLE 2

| Sample | Zinc compound | Content of zinc compound wt. %/wt. %[c] | Microbes after 24 hrs | 48 hrs | 72 hrs | 168 hrs |
|---|---|---|---|---|---|---|
| A | ZnO | 0.25/0.25 | — | — | — | — |
| B | ZnO | 0.5/0.5 | — | — | — | — |
| C | ZnO | 1.0/1.0 | — | — | — | — |
| D | ZnCl$_2$ | 0.25/0.15 | — | — | — | — |
| E | ZnCl$_2$ | 0.5/0.3 | — | — | — | — |
| F | ZnCl$_2$ | 1.0/0.6 | — | — | — | — |
| G | ZnSO$_4$[a] | 0.5/0.14 | — | — | — | — |
| H | ZnSO$_4$[a] | 1.0/0.28 | — | — | — | — |
| I | ZnSO$_4$[a] | 2.0/0.57 | — | — | — | — |
| J | Zn lactate[b] | 1.0/0.27 | — | — | — | — |
| K | Zn lactate[b] | 2.0/0.55 | — | — | — | — |

[a]in form of the heptahydrate,
[b]in form of the trihydrate,
[c]calculated as ZnO Comparative Example 1

Further, the antimicrobial activity of comparison formulations against the gram negative bacterium *Pseudomonas aeruginosa* should also be tested by the microbial count reduction test (method A). The comparison formulations used in this were prepared according to the procedure described in Example 1 and differ from the use formulations according to the invention from Table 1 only in that they contain no EVO (A-K) and/or no zinc compound (L, M).

The composition of the comparison formulations is listed in Table 3. The content by weight of the zinc compound here is in each case based on the form of the zinc compound used, i.e. on ZnO, ZnCl$_2$, ZnSO$_4$.7H$_2$O or Zn(COO—CHOH—CH$_3$)$_2$.3H$_2$O. Also stated are the corresponding quantities calculated on ZnO as reference quantity.

TABLE 3

| Sample | Zinc compound | Arlacel P 135 | Dehymuls HRE 7 | Cetiol A | Cetiol SN | Cetiol OE | Eutanol G 16 | EVO | Glycerine[a] | MgSO$_4$[b] | Zinc compound wt. %/wt. %[e] |
|---|---|---|---|---|---|---|---|---|---|---|---|
| A | ZnO | 0.8 | 3.8 | 5.3 | 6.2 | 5.3 | 2.5 | — | 5.1 | 1.0 | 0.25/0.25 |
| B | ZnO | 0.8 | 3.8 | 5.3 | 6.2 | 5.3 | 2.5 | — | 5.1 | 1.0 | 0.5/0.5 |
| C | ZnO | 0.8 | 3.8 | 5.3 | 6.2 | 5.3 | 2.5 | — | 5.1 | 1.0 | 1.0/1.0 |
| D | ZnCl$_2$ | 0.8 | 3.8 | 5.3 | 6.2 | 5.3 | 2.5 | — | 5.1 | 1.0 | 0.25/0.15 |
| E | ZnCl$_2$ | 0.8 | 3.8 | 5.3 | 6.2 | 5.3 | 2.5 | — | 5.1 | 1.0 | 0.5/0.3 |
| F | ZnCl$_2$ | 0.8 | 3.8 | 5.3 | 6.2 | 5.3 | 2.5 | — | 5.1 | 1.0 | 1.0/0.6 |
| G | ZnSO$_4$[c] | 0.8 | 3.8 | 5.3 | 6.2 | 5.3 | 2.5 | — | 5.1 | 1.0 | 0.5/0.14 |
| H | ZnSO$_4$[c] | 0.8 | 3.8 | 5.3 | 6.2 | 5.3 | 2.5 | — | 5.1 | 1.0 | 1.0/0.28 |
| I | ZnSO$_4$[c] | 0.8 | 3.8 | 5.3 | 6.2 | 5.3 | 2.5 | — | 5.1 | 1.0 | 2.0/0.57 |
| J | Zn lactate[d] | 0.8 | 3.8 | 5.3 | 6.2 | 5.3 | 2.5 | — | 5.1 | 1.0 | 1.0/0.27 |
| K | Zn lactate[d] | 0.8 | 3.8 | 5.3 | 6.2 | 5.3 | 2.5 | — | 5.1 | 1.0 | 2.0/0.55 |
| L | — | 0.8 | 3.8 | 5.3 | 6.2 | 5.3 | 2.5 | — | 5.1 | 1.0 | — |
| M | — | 0.8 | 3.8 | 5.1 | 6.0 | 5.1 | 2.5 | 2.0 | 5.0 | 1.0 | — |

[a]85 wt. %,
[b]in form of the heptahydrate,
[c]in form of the heptahydrate,
[d]in form of the trihydrate,
[e]calculated as ZnO The antimicrobial activity of the comparison formulations from Table 3 was tested in the microbial count reduction test as described in Example 1. The assessment is made as stated for method A.

Even after 168 hrs, the comparison formulations were still contaminated with *Pseudomonas aeruginosa* as can be seen from Table 4. Only comparison sample F* showed antimicrobial activity, albeit inadequate, against *Pseudomonas aeruginosa*. With this sample, sterility was only observed after 72 hrs. Thus the pronounced anti-microbial activity of the use formulation according to the invention against *Pseudomonas aeruginosa* is clearly to be attributed to a synergistic effect of the combination of EVO with zinc compound, i.e. the combination of glycerine monoalkyl ether, alkanediol, antioxidant and zinc compound (with a weight ratio (w/w) of glycerine monoalkyl ether to antioxidant of at least 10:1).

TABLE 4

| Sample | Zinc compound | Content of Zn compound wt. %/ wt. %$^d$ | Microbes after | | | |
|---|---|---|---|---|---|---|
| | | | 24 hrs | 48 hrs | 72 hrs | 168 hrs |
| A* | ZnO | 0.25/0.25 | R | ++++ | ++++ | ++++ |
| B* | ZnO | 0.5/0.5 | R | ++++ | ++++ | ++++ |
| C* | ZnO | 1.0/1.0 | R | + | + | ++ |
| D* | ZnCl$_2$ | 0.25/0.15 | R | R | R | R |
| E* | ZnCl$_2$ | 0.5/0.3 | R | R | R | R |
| F* | ZnCl$_2$ | 1.0/0.6 | R | ++ | − | − |
| G* | ZnSO$_4$$^a$ | 0.5/0.14 | R | R | R | R |
| H* | ZnSO$_4$$^a$ | 1.0/0.28 | R | R | R | R |
| I* | ZnSO$_4$$^a$ | 2.0/0.57 | R | R | R | R |
| J* | Zn lactate$_b$ | 1.0/0.27 | R | R | R | R |
| K* | Zn lactate$_b$ | 2.0/0.55 | R | R | R | R |
| L* | — | — | R | R | R | R |
| M* | — | — | R | R | R | R |

$^a$in form of the heptahydrate,
$^b$in form of the tri-hydrate,
$^c$contains EVO,
$^d$calculated as ZnO,
*comparison Example 2

The use formulations according to the invention from Table 1 were also tested for broad antimicrobial activity by a Koko test (method B). For this, each of the use formulations was inoculated and the microbial count determined for the sterility control and after each of the 6 inoculation cycles.

In addition, a comparison use formulation, sample L, which contains no zinc compound, was tested.

Surprisingly, after each inoculation cycle, no microbes could be detected any longer in the use formulations according to the invention, as is clear from Table 5. Through the combination of EVO (2 wt. % each time) with different zinc compounds in the use formulations according to the invention, pronounced antimicrobial activity against many microorganisms, i.e. broad anti-microbial activity, could be achieved, and this can already be achieved with a content of only 2.0 wt. % of EVO and only 0.15 to 1.0 wt. % of zinc compound (the quantity of zinc compound being stated as anhydrous zinc oxide), i.e. with an active substance content of only 2 to 3 wt. % overall.

TABLE 5

| Sample | Zinc compound | Content of zinc compound wt. %/ wt. %$^c$ | Sterility control | Inoculation cycles | | | | | |
|---|---|---|---|---|---|---|---|---|---|
| | | | 0 | 1 | 2 | 3 | 4 | 5 | 6 |
| A | ZnO | 0.25/0.25 | − | − | − | − | − | − | − |
| B | ZnO | 0.5/0.5 | − | − | − | − | − | − | − |
| C | ZnO | 1.0/1.0 | − | − | − | − | − | − | − |
| D | ZnCl$_2$ | 0.25/0.15 | − | − | − | − | − | − | − |
| E | ZnCl$_2$ | 0.5/0.3 | − | − | − | − | − | − | − |
| F | ZnCl$_2$ | 1.0/0.6 | − | − | − | − | − | − | − |
| H | ZnSO$_4$$^a$ | 1.0/0.28 | − | − | − | − | − | − | − |
| I | ZnSO$_4$$^a$ | 2.0/0.57 | − | − | − | − | − | − | − |
| J | Zn lactate$^b$ | 1.0/0.27 | − | − | +++$_B$ | − | − | − | − |
| K | Zn lactate$^b$ | 2.0/0.55 | − | − | − | − | − | − | − |
| L* | — | — | − | +++$_B$ | +++$_B$ | − | − | − | − |

$^a$in form of the heptahydrate,
$^b$in form of the trihydrate,
$^c$calculated as ZnO
*comparison Example 3

Further, formulations were tested for broad anti-microbial activity using the Koko test (method B). The formulations used in this were prepared according to the procedure described in Example 1 and apart from the different zinc content differ from the use formulations according to the invention from Table 1 only in that they contain no EVO (samples A, D and G) or the EVO is replaced by EV (samples B, C, E, F, H and I).

The composition of the comparison formulations is listed in Table 6. The content by weight of the zinc compound here is in each case based on the form of the zinc compound used, i.e. on ZnO, ZnCl$_2$ or ZnSO$_4$.7H$_2$O. Also stated are the corresponding quantities calculated on anhydrous zinc oxide as reference quantity.

The formulations from Table 6 were tested for antimicrobial activity in the Koko test. In this, the respective comparison formulations were inoculated and the microbial count determined for the sterility control and after each of the 6 inoculation cycles.

The results presented in Table 7 show that the addition of glycerine monoalkyl ether and antioxidant to zinc compound markedly improves the activity.

TABLE 6

| | | Content (wt. %) | | | | | | | | | |
|---|---|---|---|---|---|---|---|---|---|---|---|
| Sample | Zinc compound | Arlacel P 135 | Dehymuls HRE 7 | Cetiol A | Cetiol SN | Cetiol OE | Eutanol G 16 | EV | Glycerine$^a$ | MgSO$_4$$^b$ | Zinc compound wt. %/wt. %$^d$ |
| A | ZnO* | 0.8 | 3.8 | 5.3 | 6.2 | 5.3 | 2.5 | — | 5.1 | 1.0 | 0.13/0.13 |
| B | ZnO | 0.8 | 3.8 | 5.2 | 6.1 | 5.2 | 2.5 | 1.5 | 5.0 | 1.0 | 0.13/0.13 |
| C | ZnO | 0.8 | 3.8 | 5.1 | 6.0 | 5.1 | 2.5 | 2.0 | 5.0 | 1.0 | 0.13/0.13 |

TABLE 6-continued

| Sample | Zinc compound | Arlacel P 135 | Dehymuls HRE 7 | Cetiol A | Cetiol SN | Cetiol OE | Eutanol G 16 | EV | Glycerine[a] | MgSO$_4$[b] | Zinc compound wt. %/wt. %[d] |
|---|---|---|---|---|---|---|---|---|---|---|---|
| D | ZnCl$_2$* | 0.8 | 3.8 | 5.3 | 6.2 | 5.3 | 2.5 | — | 5.0 | 1.0 | 0.22/0.13 |
| E | ZnCl$_2$ | 0.8 | 3.8 | 5.2 | 6.1 | 5.2 | 2.5 | 1.5 | 5.0 | 1.0 | 0.22/0.13 |
| F | ZnCl$_2$ | 0.8 | 3.8 | 5.1 | 6.0 | 5.1 | 2.5 | 2.0 | 5.0 | 1.0 | 0.22/0.13 |
| G | ZnSO$_4$[c]* | 0.8 | 3.8 | 5.3 | 6.2 | 5.3 | 2.5 | — | 5.1 | 1.0 | 0.46/0.13 |
| H | ZnSO$_4$[c] | 0.8 | 3.8 | 5.2 | 6.1 | 5.2 | 2.5 | 1.5 | 5.0 | 1.0 | 0.46/0.13 |
| I | ZnSO$_4$[c] | 0.8 | 3.8 | 5.1 | 6.0 | 5.1 | 2.5 | 2.0 | 5.0 | 1.0 | 0.46/0.13 |

Content (wt. %)

[a] 85 wt. %,
[b] in form of the heptahydrate,
[c] in form of the heptahydrate,
[d] calculated as ZnO
*comparison formulation (no glycerine ether and no antioxidant contained)

TABLE 7

| Sample | Zinc compound | Content of zinc compound wt. %/wt. %[b] | EV content [wt. %] | Sterility control 0 | 1 | 2 | 3 | 4 | 5 | 6 |
|---|---|---|---|---|---|---|---|---|---|---|
| A | ZnO | 0.13/0.13 | — | − | +++$_B^{HS}$ | +++$_B^{HS}$ | ./. | | | |
| B | ZnO | 0.13/0.13 | 1.5 | − | ++$_S$ | +$_S$ | − | − | ++$_S$ | ++$_S$ |
| C | ZnO | 0.13/0.13 | 2 | − | +$_S$ | − | − | +$_{1S}$ | − | − |
| D | ZnCl$_2$ | 0.22/0.13 | — | − | +++$_B^S$ | +++$^S$ | ./. | | | |
| E | ZnCl$_2$ | 0.22/0.13 | 1.5 | − | ++$_S$ | +$_S$ | − | +$_{2S}$ | +$_S$ | ++$_S$ |
| F | ZnCl$_2$ | 0.22/0.13 | 2 | − | ++$_S$ | +$_S$ | − | +$_{2S}$ | +$_S$ | +++$_S$ |
| G | ZnSO$_4$[a] | 0.46/0.13 | — | − | ++$_B^S$ | +++$_B^S$ | +++$_B^S$ | ./. | | |
| H | ZnSO$_4$[a] | 0.46/0.13 | 1.5 | − | ++$_S$ | +$_S$ | +$_S$ | +$_S$ | +++$_B^{HS}$ | +++$_B^S$ |
| I | ZnSO$_4$[a] | 0.46/0.13 | 2 | − | ++$_S$ | +$_S$ | + | +$_S$ | ++$_S$ | ++$_S$ |

Inoculation cycles

[a] in form of the heptahydrate,
[b] calculated as ZnO

Example 4

In addition, the stability of concentrates was tested. Concentrates B and C are comparison concentrates, concentrates A and D are according to the invention.

TABLE 8

(Composition of concentrates)

| A | Zinc chloride | Water | EV |
|---|---|---|---|
| Ratio wt. %/wt. %[a] | 1 19.05/11.37 | 4.76 | 4 76.19 |

| B* | Zinc chloride | Water | 2-ethylhexyl glycerine ether |
|---|---|---|---|
| Ratio wt. %/wt. %[a] | 1 19.05/11.37 | 4.76 | 4 76.19 |

| C* | Zinc chloride | Propylene glycol | 2-ethylhexyl glycerine ether |
|---|---|---|---|
| Ratio wt. %/wt. %[a] | 1 8.33/4.97 | 25.00 | 8 66.66 |

| D | Zinc chloride | Propylene glycol | EV |
|---|---|---|---|
| Ratio wt. %/wt. %[a] | 1 8.33/4.97 | 25.00 | 8 66.66 |

[a]Calculated as ZnO

TABLE 9

(Stability test)

| | 40° C. | | | 60° C. | | |
|---|---|---|---|---|---|---|
| | null value | 1 week | 1 month | null value | 1 week | 1 month |
| Colour No. (Hazen) | | | | | | |
| A | 29 | 23 | 32 | 29 | 40 | 84 |
| B* | 22 | 23 | 100 | 22 | 156 | 796 |
| C* | 13 | 14 | 75 | 13 | 85 | 159 |
| D | 18 | 20 | 16 | 18 | 16 | 21 |
| Appearance | | | | | | |
| A | liquid, clear, pale yellowish | liquid, clear, pale yellowish | liquid, clear, pale yellowish | liquid, clear, pale yellowish | liquid, clear, yellowish | liquid, clear, yellowish |
| B* | liquid, clear almost colourless | liquid, clear, yellowish | liquid, clear, yellowish | liquid, clear almost colourless | liquid, clear, yellow | liquid, clear, dark yellow |
| C* | liquid, clear almost colourless | liquid, clear almost colourless | liquid, clear, yellowish | liquid, clear almost colourless | liquid, clear, yellow | liquid, clear, yellow |
| D | liquid, clear almost colourless | liquid, clear almost colourless, quite pale, more yellowish than C | liquid, clear almost colourless | liquid, clear almost colourless | liquid, clear almost colourless | liquid, clear, pale yellowish |

*comparison

From the above data, it follows that the concentrates A and D according to the invention are very much more stable (in particular more colour-stable) than the comparison concentrates B and C. Concentrate D with a content of diol is particularly preferable, as it is particularly stable.

Example 5

Further, the action of combinations according to the invention against the caries-causing organism *Streptococcus mutans* in the mouthwash formulations shown in Table 10 was tested. The MIC values determined according to method C are shown in Table 11 below.

TABLE 10

(Mouthwash)

| | | Content (wt. %) | | | | |
|---|---|---|---|---|---|---|
| Sample | Zinc compound | Mghs | EV | water | Zinc compound wt. %/wt. %[a] | |
| A* | — | 0.5 | — | qsp 100 | — | |
| B | — | 0.5 | 0.2 | qsp 100 | — | |
| C* | ZnCl$_2$ | 0.5 | 0 | qsp 100 | 1.0/0.6 | |
| D | ZnCl$_2$ | 0.5 | 0.2 | qsp 100 | 0.2/0.12 | |
| E | ZnCl$_2$ | 0.5 | 0.4 | qsp 100 | 0.2/0.12 | |
| F | ZnCl$_2$ | 0.5 | 0.2 | qsp 100 | 1.0/0.6 | |
| G | ZnCl$_2$ | 0.5 | 0.4 | qsp 100 | 1.0/0.6 | |
| H* | TZC | 0.5 | — | qsp 100 | 0.2/0.026 | |
| I | TZC | 0.5 | 0.2 | qsp 100 | 0.2/0.026 | |
| J | TZC | 0.5 | 0.4 | qsp 100 | 0.2/0.026 | |

*comparison,
[a]Calculated as ZnO

The pH of the formulations was adjusted to pH 4.

TABLE 11

| Sample | *Streptococcus mutans* ATCC: 25175 (MIC) wt. %/wt. %[a] |
|---|---|
| A* | >0.25 Mghs |
| B | >0.1 EV |
| | >0.25 Mghs |

TABLE 11-continued

| Sample | *Streptococcus mutans* ATCC: 25175 (MIC) wt. %/wt. %[a] | |
|---|---|---|
| C* | 0.125/0.075 | $ZnCl_2$ |
|  | 0.0675 | Mghs |
| D | 0.05 | EV |
|  | 0.05/0.03 | $ZnCl_2$ |
|  | 0.125 | Mghs |
| E | 0.05 | EV |
|  | 0.025/0.015 | $ZnCl_2$ |
|  | 0.0675 | Mghs |
| F | 0.025 | EV |
|  | 0.125/0.075 | $ZnCl_2$ |
|  | 0.0675 | Mghs |
| G | 0.05 | EV |
|  | 0.125/0.075 | $ZnCl_2$ |
|  | 0.0675 | Mghs |
| H* | >0.1/0.013 | TZC |
|  | >0.25 | Mghs |
| I | 0.05 | EV |
|  | 0.05/0.006 | TZC |
|  | 0.125 | Mghs |
| J | 0.05 | EV |
|  | 0.025/0.003 | TZC |
|  | 0.0675 | Mghs |

*comparison,
[a]converted to ZnO

In the 1:1 ratio, the combination of zinc salt and EV enables the reduction of the individual substances, and even in the ratio 1:2, the total active substance can be decreased. Due to the low water solubility, the activity of the zinc citrate (TZC) is not sufficient. Through addition of EV, effective combinations in the range of the solubility of TZC are formed.

Sample A shows that the matrix does not have intrinsic activity. The solubilizer Mghs is also always run for completeness, but has no intrinsic activity (according to sample A).

The invention claimed is:

1. Antimicrobial composition in the form of a concentrate, the active ingredients of the composition consisting of:
   (i) 0.1 to 50 wt. % of at least one zinc compound selected from zinc salt and zinc oxide, where the quantity of zinc compound is stated as anhydrous zinc oxide;
   (ii) 10 to 90 wt. % of at least one glycerine monoalkyl ether of the general formula R—O—$CH_2$—CHOH—$CH_2OH$,
   wherein R is a branched or unbranched $C_1$-$C_{24}$ alkyl group, wherein the alkyl group can be substituted with one or more hydroxy and/or $C_1$-$C_4$ alkoxy group(s) and/or the alkyl chain can be interrupted by up to four oxygen atoms; and
   (iii) $10^{-4}$ to 0.9 wt. % of at least one antioxidant; and optionally
   (iv) one or more alkanediols.

2. The composition according to claim 1, further comprising (iv) one or more alkanediols.

3. The composition according to claim 1, wherein the zinc compound is selected from the group consisting of zinc oxide, zinc chloride, zinc sulphate, zinc phosphate, zinc carbonate, zinc pyrithione, zinc ascorbate, zinc dehydracetate, zinc carboxylate, zinc lactate, zinc citrate, zinc stearate, zinc hydroxystearate, zinc benzoate, zinc sorbate, zinc salicylate, zinc gluconate, zinc ricinoleate, zinc undecylenate GP and zinc pyrrolidone-carboxylate.

4. The composition according to claim 1, wherein R possesses 3 to 20 carbon atoms.

5. The composition according to claim 1, wherein the weight ratio (w/w) of component (i) to component (ii) is in the range of from 20:1 to 1:400, wherein the quantity of zinc compound is stated as anhydrous zinc oxide.

6. The composition according to claim 2, wherein the alkanediol is a 1,2-alkanediol which has 2 to 18 carbon atoms.

7. The composition according to claim 2, wherein the weight ratio (w/w) of component (i) to component (iv) is in the range of from 1:50 to 5:1, wherein the quantity of zinc compound is stated as anhydrous zinc oxide.

8. The composition according to claim 2, wherein the weight ratio (w/w) of component (ii) to component (iv) is 10:1 to 1:10.

9. The composition according to claim 1, wherein the antioxidant is selected from the group consisting of 3-tert-butyl-4-hydroxyanisole, 2,6-ditert-butyl-p-cresol, toco-pherol, vitamin E and derivatives thereof, p-hydroxybenzoic acid esters, dimethyloldimethylhydantoin, and N-acylamino acids and salts thereof.

10. The composition according to claim 1, wherein the weight ratio (w/w) of component (ii) to component (iii) is at least 100:1.

11. The composition according to claim 1,
   (i)
   (ii)
   (iii)
   (iv) further comprising 10 to 90 wt. % of alkanediol.

12. Method for the production of the composition according to claim 1 in the form of a concentrate, comprising:
   providing component (i) in solvent, and
   adding component (ii), optionally in combination with component (iii), and if present component (iv), to component (i).

13. A method for the treatment of a microbially caused disease, comprising administrating to a subject in need thereof an effective amount of the antimicrobial composition according to claim 1.

14. A method of controlling bacteria, yeasts, fungi, viruses and/or protozoa on human skin or mucous membrane, comprising administering to a subject in need thereof an effective amount of the antimicrobial composition according to claim 1.

15. The composition according to claim 1, wherein R is 2-ethylhexyl.

16. The composition according to claim 2, wherein the alkanediol is 1,2-octanediol.

17. The composition according to claim 1, wherein the antioxidant is vitamin E.

18. The composition according to claim 1, wherein the active ingredients consist of:
   (i) 2 to 30 wt. % of zinc compound, where the quantity of zinc compound is stated as anhydrous zinc oxide,
   (ii) 14 to 30 wt. % of glycerine monoalkyl ether,
   (iii) 0.006 to 0.02 wt. % of antioxidant, and optionally
   (iv) 33 to 65 wt. % of alkanediol.

* * * * *